United States Patent [19]
Miyake et al.

[11] Patent Number: 5,145,850
[45] Date of Patent: Sep. 8, 1992

[54] IMIDAZOPYRIDAZINES, THEIR PRODUCTION AND USE

[75] Inventors: Akio Miyake, Hirakata; Yasuko Ashida, Takatsuki, both of Japan

[73] Assignee: Takeda Chemical Industries, Ltd., Osaka, Japan

[21] Appl. No.: 659,704

[22] Filed: Feb. 25, 1991

[30] Foreign Application Priority Data

Mar. 1, 1990 [JP] Japan .................................. 2-051072
Dec. 28, 1990 [JP] Japan .................................. 2-418682

[51] Int. Cl.$^5$ .................... A61K 31/50; A61K 31/535; A61K 31/55; C07D 487/04
[52] U.S. Cl. .................... 514/248; 514/210; 514/218; 514/228.5; 514/233.2; 540/575; 540/599; 544/61; 544/117; 544/236; 549/426; 549/497; 549/511; 558/15; 558/16; 560/250; 564/80
[58] Field of Search .................. 544/236, 117, 61; 540/575, 599; 514/248, 218, 233.2, 210, 212, 228.5

[56] References Cited

U.S. PATENT DOCUMENTS 4,464,372  8/1984  Bristol et al. .................... 544/236

FOREIGN PATENT DOCUMENTS 0160252  11/1985  European Pat. Off. .
0203271  12/1986  European Pat. Off. .
225522   6/1987   European Pat. Off. .
0305093  3/1989   European Pat. Off. .
0381132  8/1990   European Pat. Off. .

OTHER PUBLICATIONS

Miyake et al, Chemical Abstracts, vol. 114, No. 102028 (1990) (Abstract for EP 381132).
Abstract for JP 01040489 (Feb. 10, 1989).

*Primary Examiner*—Mukund J. Shah
*Assistant Examiner*—E. Bernhardt
*Attorney, Agent, or Firm*—Wegner, Cantor, Mueller & Player

[57] ABSTRACT

An imidazo [1,2-b]pyridazine compound of the formula (I):

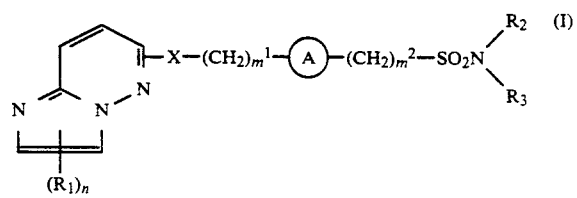

wherein $R_1$ is a halogen atom or a lower alkyl group optionally having substituent(s), $R_2$ and $R_3$ are, independently, a hydrogen atom, a lower alkyl group optionally having substituent(s), a cycloalkyl group or a phenyl group optionally having substituent(s) or $R_2$ and $R_3$ together with the adjacent nitrogen atom to which they bond may form a heterolcyclic ring optionally having substituent(s), X is an oxygen atom or $S(O)_k$ (k is zero to two), a group —Ⓐ— is a bivalent three to seven membered homocyclic or heterocyclic group optionally having substituent(s), $m^1$ and $m^2$ each is an integer of 0 to 4 and n is an integer of 0 or 1; or its salt, which is useful as antiasthmatics.

16 Claims, No Drawings

IMIDAZOPYRIDAZINES, THEIR PRODUCTION AND USE

BACKGROUND OF THE INVENTION

1. Field of the Invention

This invention relates to novel imidazopyridazine derivatives, their production and use.

The imidazopyridazine derivatives of the invention possess antiallergic, anti-inflammatory and anti-PAF (platelet-activating factor) activities and are useful as antiasthmatics by controlling bronchospasm and bronchoconstriction.

2. Description of the Prior Art

It has been disclosed in Japanese Unexamined Patent Publication No. SHO 61(1986)-152684 that imidazo[1,2-b]pyridazine compounds show anti-thrombogenic activity as well as cardiovascular activity, especially cardiotonic activity. However, any imidazo[1,2-b]pyridazine derivative possessing antiallergic, anti-inflammatory and anti-PAF activities has not been reported.

On the other hand, it is desired to develop more effective antiasthmatics, although various kinds of antiasthmatics have been launched into markets.

As the result of extensive studies on chemical modification at the 6 position of imidazo[1,2-b] pyridazine, the inventors of this invention have found imidazo[1,2-b]pyridazine derivatives possessing antiallergic, anti-inflammatory and anti-PAF activities which are not reported so far in the existing imidazo[1,2-b]pyridazine compounds. Said derivatives have been also found to control bronchospasm and bronchoconstriction.

Thus, this invention has been completed.

SUMMARY OF THE INVENTION

The invention provides an imidazo[1,2-b]pyridazine compound of the formula (I):

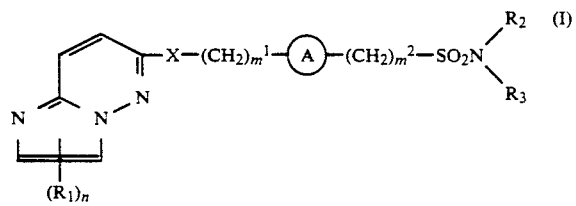

wherein $R_1$ is a halogen atom or a lower alkyl group optionally having substituent(s), $R_2$ and $R_3$ are, independently, a hydrogen atom, a lower alkyl group optionally having substituent(s), a cycloalkyl group or a phenyl group optionally having substituent(s) or $R_2$ and $R_3$ together with the adjacent nitrogen atom to which they bond may form a heterocyclic ring optionally having substituent(s), X is an oxygen atom or $S(O)_k$ (k is zero to two), a group -Ⓐ- is a bivalent three to seven membered homocyclic or heterocyclic group optionally having substituent(s), $m^1$ and $m^2$ each is an integer of 0 to 4 and n is an integer of 0 or 1; or its salt.

Further, it provides a process for the production of the above-mentioned compound and a pharmaceutical composition containing said compound. When the compounds of the formula (I) contain an asymmetric carbon atom, their optically active compounds and racemic mixtures are also included in the invention.

PREFERRED EMBODIMENTS OF THE INVENTION

The term "lower alkyl group" as used in the specification means a straight or branched chain alkyl group containing one to six carbon atoms. Examples of the lower alkyl groups are methyl, ethyl, n-propyl, i-propyl, n-butyl, i-butyl, tert-butyl, n-pentyl and n-hexyl.

The term "cycloalkyl group" means a cycloalkyl group containing three to six carbon atoms. Examples of the cycloalkyl groups are cyclopropyl, cyclobutyl, cyclopentyl and cyclohexyl.

Examples of the substituents in the lower alkyl group having optionally substituent(s) are hydroxy, amino, a mono-lower alkylamino having, for example, one to four carbon atoms such as methylamino or ethylamino, a lower alkoxy having, for example, one to four carbon atoms such as methoxy or ethoxy and a halogen. The number of such substituents is one to four. Examples of the substituents in the phenyl group optionally having substituent(s) are amino, a mono-lower alkylamino as mentioned above or a di-lower alkylamino such as di-$C_{1-4}$ alkylamino (e.g., dimethylamino or diethylamino), a lower alkoxy having, for example, one to four carbon atoms such as methoxy or ethoxy and a halogen. The number of such substituents is one to five.

A fluorine, chlorine, bromine or iodine atom is used for a halogen atom.

The heterocyclic ring in the case where $R_2$ and $R_3$ together with the nitrogen atom to which they bond form a heterocyclic ring means a four to seven membered heterocyclic ring having at least one nitrogen atom and optionally an oxygen and/or sulfur atoms therein. A five or six membered heterocyclic ring is normally preferable. Examples of the five or six membered heterocyclic rings are pyrrolidino, piperidino, morpholino, piperazino and homopiperazino. These five to six membered heterocyclic rings may be substituted by one to five of substituents exemplified as those for the lower alkyl and phenyl groups.

Preferably, n is 0 or $R_1$ is a methyl group, and $R_2$ and $R_3$ are a hydrogen atom and so on. Preferably, X is an oxygen or sulfur atom. Preferably, $m^1$ and $m^2$ are, for example, one to three.

A group —A— may be a bivalent three to seven membered homocyclic or heterocyclic group optionally having substituent(s). The homocyclic groups include monocyclic, saturated or unsaturated $C_{3-7}$ hydrocarbon groups, and the heterocyclic groups include three to seven membered ones having at least one oxygen, sulfur or nitrogen atom as a constituent atom of the ring. These groups may be bivalent groups obtained by removing two hydrogen atoms which bond to one carbon atom on the ring or removing one hydrogen atom which bonds to one carbon atom on the ring and one hydrogen atom which bonds to another carbon atom thereon.

Examples of the homocyclic groups are bivalent groups obtained by removing two hydrogen atoms from one or two carbon atoms of $C_{3-7}$ monocyclic hydrocarbons such as cyclopropane, cyclobutane, cyclopentane, cyclohexane, cyclopentene, cyclohexene, cyclohexadiene or benzene. Specifically, such groups are as follows:

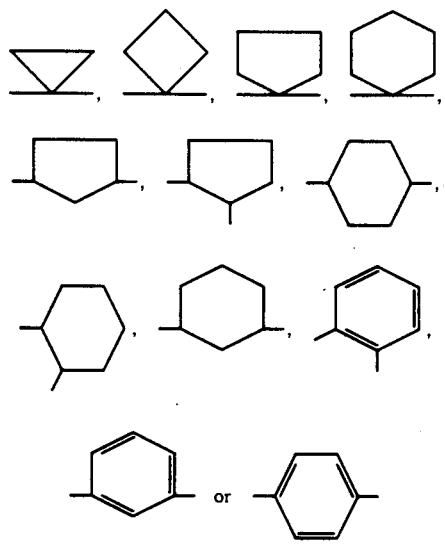

Examples of the heterocyclic groups are bivalent groups obtained by removing two hydrogen atoms from one or two constituent atoms of three to seven membered saturated or unsaturated heterocyclic groups having one to four sulfur, nitrogen or oxygen atoms, such as oxetane, tetrahydrofuran, furan, dihydrothiophene, tetrahydrothiophene, thiophene, azetidine, pyrrolidine, pyrrole, tetrahydropyran, pyran, thiopyran, piperidine, pydridine, thiazole, imidazole or pyrimidine. Specifically, such groups are as follows:

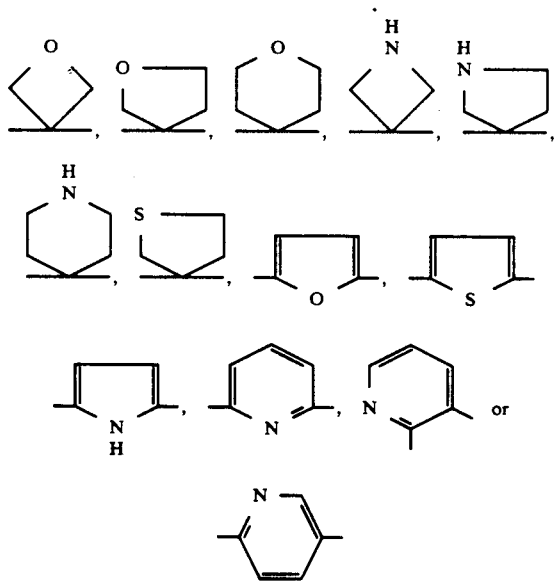

Examples of the substituents on the homocyclic or heterocyclic groups are a lower alkyl group optionally having substituent(s), an amino group, a substituted amino group, an amido group, a substituted amido group, a hydroxy group, or a lower alkoxy group (e.g., a $C_{1-4}$ alkoxy group such as methoxy or ethoxy) and a halogen atom (e.g., chlorine, bromine, iodine or fluorine atom). The number of the substituents is one to five. The lower alkyl groups optionally having substituent(s) include those used for $R_1$ as mentioned above. Examples of the substituted amino groups are a mono-$C_{1-4}$ alkyl-amino group such as methylamino, ethylamino or propylamino, a di-$C_{1-4}$ alkylamino group such as dimethylamino or diethylamino or a five to seven membered cyclic amino group such as pyrrolidino, morpholino or piperazino. Examples of the substituted amido groups are $C_{1-4}$ acylamido groups such as acetamido, propioamido or butyramido.

Preferable examples of the compounds (I) or their salts are compounds or their salts represented by the following formulas:

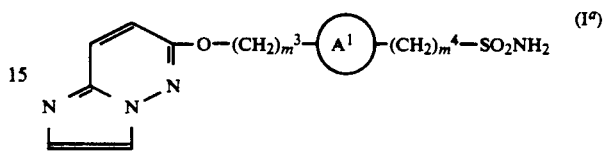

wherein a group $-(A^1)-$ represents a three to six membered cycloalkylene group and $m^3$ and $m^4$ each represents an integer of 1 or 2; and

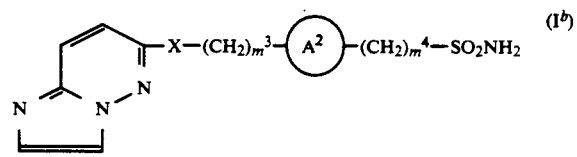

wherein X represents an oxygen or sulfur atom, a group $-(A^2)-$ represents

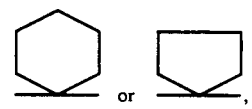

and other symbols have the same meanings as defined above.

The compound (I) or its salt of thin invention can be obtained A) by reacting a compound of the formula (II):

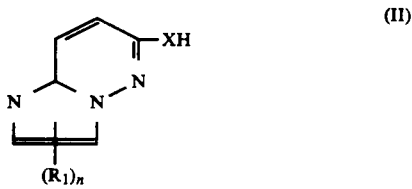

or its salt with a compound of the formula (III):

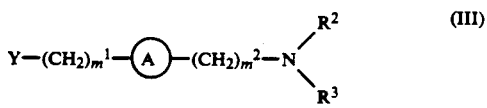

or its salt.

The symbols used in the above formulas have the same meanings as defined above, except that Y in the formula (III) represents a reactive group.

Examples of the reactive groups of Y in the formula (III) are a halogen (e.g., chlorine, iodine or bromine), a $C_{6-10}$ arylsulfonyloxy (e.g., benzenesulfonyloxy or p- toluenesulfonyloxy) and a $C_{1-4}$ alkylsulfonyloxy (e.g., methanesulfonyloxy).

The reaction can be advantageously conducted in the presence of a base. Examples of the bases are an alkali metal hydride (e.g., sodium hydride or potassium hydride), an alkali metal alkoxide (e.g., sodium methoxide or sodium ethoxide), a hydroxide compound (e.g., sodium hydroxide or potassium hydroxide) and a carbonate compound (e.g., sodium carbonate or potassium carbonate).

This reaction is usually carried out in an inert solvent such as an alcohol (e.g., methanol or ethanol), an ether (e.g., dioxane or tetrahydrofuran), an aromatic hydrocarbon (e.g., benzene, toluene or xylene), a nitrile (e.g., acetonitrile), an amide (e.g., dimethylformamide or dimethylacetamide) and a sulfoxide (e.g., dimethyl sulfoxide). The reaction temperature is usually about 10° to 200° C., preferably about 50° to 100° C. The reaction time is usually about 30 minutes to 24 hours, preferably about 1 to 6 hours.

The product of this reaction can be isolated and purified by the known methods such as solvent extraction, change of basicity, redistribution, salting out, crystallization, recrystallization or chromatography.

Furthermore, the compound (I) or its salt of this invention can be obtained B) by reacting a compound of the formula (IV):

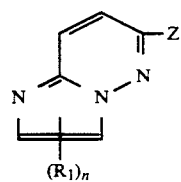

or its salt with a compound of the formula (V):

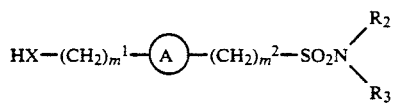

or its salt.

The symbols used in the above formulas have the same meanings as defined in the formula (I), except that Z in the formula (IV) means a reactive group.

The condensation reaction can be also advantageously conducted in the presence of a base.

The reactive groups and bases described in the aforementioned method A) are also applicable to those employed as Z in the formula (IV) and employed in the condensation reaction, respectively.

This reaction can be usually carried out in an inert solvent such as an alcohol (e.g., methanol or ethanol), an ether (e.g., dioxane or tetrahydrofuran), an aromatic hydrocarbon (e.g., benzene, toluene or xylene), a nitrile (e.g., acetonitrile), an amide (e.g., dimethylformamide or dimethylacetamide) or a sulfoxide (e.g., dimethyl sulfoxide) at about 10° to 200° C., preferably 50° to 150° C. for 30 minutes to 24 hours, preferably 1 to 10 hours. The product can be isolated and purified by the known methods such as solvent extraction, change of basicity, redistribution, salting out, crystallization, recrystallization or chromatography.

Further, the compound (I) or its salt can be obtained C) by reacting a compound of the formula (VI):

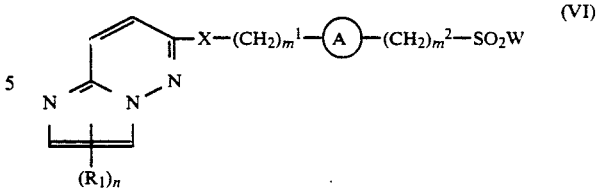

wherein the symbols have the same meanings as in the formula (I), except that W represents a halogen atom, or its salt with an amine of the formula (VII):

wherein $R_2$ and $R_3$ each represents the same meanings as defined in the formula (I) or its salt.

This reaction can be usually carried out in an inert solvent, e.g., an alcohol (e.g., methanol, ethanol), an ether (e.g., dioxane, tetrahydrofuran), a halogenated hydrocarbon (e.g., dichloromethane or chloroform), a nitrile (e.g., acetonitrile), or a sulfoxide (e.g., dimethyl sulfoxide), at about −20° to 100° C., preferably at about −10° to 50° C. for about 30 minutes to 5 hours, preferably for about 1 to 3 hours. The product can be isolated and purified by the known methods such as solvent extraction, change of basicity, redistribution, salting out, crystallization, recrystallization or chromatography.

The compounds (I) thus obtained can be converted, if desired, to its corresponding salts by the conventional method.

The salts of the compounds (I) of this invention are suitable pharmaceutically or physiologically acceptable salts. Examples of such salts are the salts with an inorganic acid such as hydrochloric acid, sulfuric acid or phosphoric acid, or with an organic acid such as methanesulfonic acid, p-toluenesulfonic acid, fumaric acid, lactic acid, tartaric acid or citric acid. These salts are also usable as the salts of the compounds (II), (III), (IV), (V), (VI) and (VII), which are used as the starting materials for producing the compounds (I).

As for the starting materials to be employed in the method for producing the compounds (I) or salts thereof, the compounds (II) can be prepared by the method of Reference Example 1 stated below or analogous ones thereto; the compounds (III) can be prepared by the methods disclosed e.g., in Chem. Ber. 91, 2130 (1958), J. Org. Chem. 52, 2162 (1987) and Japanese Unexamined Patent Publication No. SHO 62(1987)-48687 or analogous ones thereto or by the method of Reference Example 2 stated below or analogous ones thereto; the compounds (IV) can be prepared by the methods disclosed e.g., in Tetrahedron 24, 239 (1968) or analogous ones thereto; the compounds (V) can be prepared by converting a reactive group Y of the compounds (III) into mercapto or hydroxy group in accordance with the conventional methods. The compounds (V) where X is O can be prepared from the starting materials (VIII) disclosed in J. Org. Chem. 24, 1839 (1960) by the following reaction scheme or analogous ones thereto.

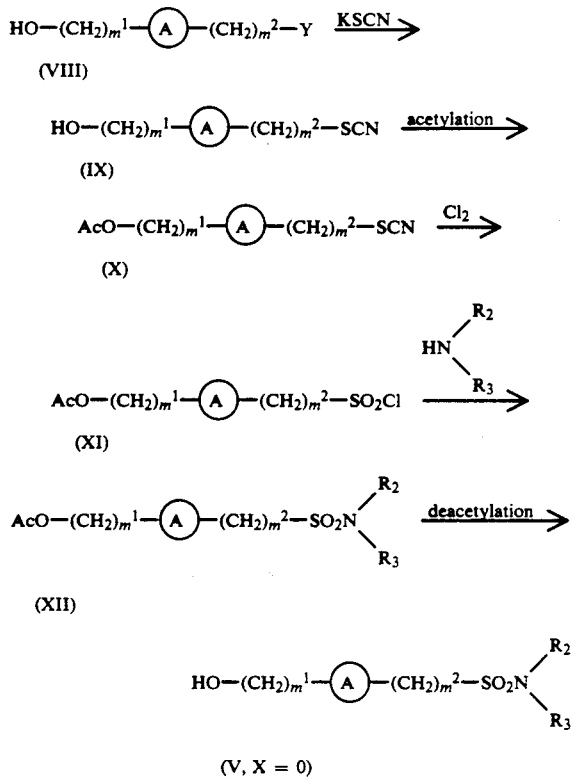

In the above formulas, the symbols have the same meanings as defined above and Ac is an acetyl group. Further, the compound (VI) can be prepared by reacting a compound (II) or its salt with a compound of the formula:

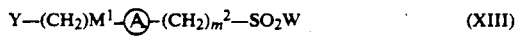

wherein the symbols have the same meanings as defined above, or reacting a compound (IV) or its salt with a compound of the formula:

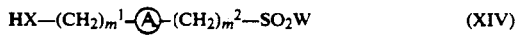

wherein the symbols have the same meanings as defined above.

When the compound (I) or its pharmaceutically acceptable salt is administered as an antiasthmatic agent to mammals, e.g., humans, the dosage varies depending upon the age, body weight, status of disease, route of administration, frequency of administration, etc., but is generally 0.1 to 100 mg/Kg/day, preferably 1 to 50 mg/Kg/day as divided into two to three times a day.

The administration route may be oral or parenteral.

The compound (I) of this invention or its salt can be administered as it is, but usually in the form of a pharmaceutical preparation which is prepared together with a pharmaceutically acceptable carrier or diluent. Examples of the pharmaceutical preparations are tablets, capsules, granules, fine granules, powders, syrups, injections or inhalations. These preparations can be prepared by the conventional methods. Examples of the carriers for the oral preparations are starch, mannite, crystalline cellulose and sodium carboxymethylcellulose, which are commonly used in the pharmaceutical preparations. As the carriers to be employed for injections, there are distilled water, physiological saline solution, glucose solution and infusion agent. Other additives which are conventionally used in the pharmaceutical preparations may be suitably added to the above mentioned preparations.

REFERENCE EXAMPLE 1

Production of 6-mercaptoimidazo[1,2-b]pyridazine

6-Chloroimidazo[1,2-b]pyridazine (13.5 g), 28 W/W% sodium methoxide-methanol solution (17.5 g) and thioacetic acid (7.0 g) were dissolved in 70 ml of methanol and this solution was heated at 150° C. in a sealed tube for 6 hours. The reaction mixture was cooled to room temperature and distilled to remove the organic solvent. The residue was washed three times with chloroform (50 ml), and the insoluble material was extracted six times with 50 ml of chloroform-methanol (1:1) solution. The combined extracts were distilled to remove the organic solvent. The precipitated crystals were collected by filtration, thereby obtaining 6-mercaptoimidazo[1,2-b]pyridazine (3.7 g).

Elementary analysis: $C_6H_5N_3S$: Calculated (%): C, 47.11; H, 3.43; N, 27.47. Found (%): C, 46.97; H, 3.25; N, 27.25.

REFERENCE EXAMPLE 2

Production of 3-hydroxy-2,2-pentamethylene-1-propanesulfonamide a) A mixture of 3-bromo-2,2-pentamethylene-1-propanol (4.6 g), potassium thiocyanate (4.6 g) and dimethylformamide (15 ml) was stirred for 16 hours at 110° C., and then, stirred for 2 hours at 130° C. under heating. The reaction solution was poured into ice water and extracted with ethyl acetate (100 ml×2). The extract was washed with saturated saline, dried over anhydrous magnesium sulfate and distilled to remove the solvent. The residue was subjected to a silica gel column chromatography, eluting with hexane-ethyl acetate (3:1). The corresponding fractions were concentrated to obtain 3-hydroxy-2,2-pentamethylene-1-propanethiocyanate as colorless oil (2.6 g).

NMR(CDCl$_3$)δ: 1.47(10H,s), 1.65(1H,t,J=4Hz), 3.18(2H,s), 3.58(2H,d,J=4Hz)

b) 3-Hydroxy-2,2-pentamethylene-1-propanethiocyanate (1.5 g) was dissolved in acetic anhydride (1.53 ml), to which pyridine (1.31 ml) was added. The mixture was reacted for 2 hours at room temperature, and then concentrated under reduced pressure. The residue was subjected to a silica gel column chromatography, eluting with hexane-ethyl acetate (6:1). The corresponding fractions were concentrated to obtain 3-acetoxy-2,2-pentamethylene-1-propanethiocyanate as colorless oil (1.7 g).

NMR(CDCl$_3$)δ: 1.49(10H,s), 2.09(3H,s), 3.14(2H,s), 4.05(2H,s)

c) Water (30 ml) was added to a solution of 3-acetoxy-2,2-pentamethylene-1-propanethiocyanate (6.8 g) in acetic acid (30 ml), in which chlorine gas was bubbled for 3 hours at room temperature, while stirring. The reaction solution was concentrated under reduced pressure, to which ice water (100 ml) was added. The resultant solution was extracted with dichloromethane (200 ml). The extract was washed with water, dried and concentrated under reduced pressure. The residue was dissolved into dichlomethane (50 ml), in which ammonia gas was bubbled for an hour. The reaction solution was poured into ice water (100 ml). The organic layer was collected and the aqueous layer was extracted with dichloromethane (50 ml×5). The extract was washed with a saturated saline, dried over anhydrous magnesium sulfate and concentrated under reduced pressure. Thereafter, the residue was subjected to a silica gel column chromatography, eluting with hexane-ethyl acetate (1:1). The corresponding fractions were concentrated to obtain 3-acetoxy-2,2-pentamethylene-1-sulfonamide as colorless oil (5.0 g).

NMR(CDCl$_3$)δ: 1.3–1.8(10H,m), 2.09(3H,s), 3.33(2H,s), 4.25(2H,s), 4.98(2H,s)

d) 3-Acetoxy-2,2-pentamethylene-1-propanesulfonamide (5.0 g) was dissolved into methanol (20 ml), to which 1 N-sodium methoxide mathanol (24 ml) was added and stirred for an hour at room temperature (15° C.). After adding acetic acid (1.38 ml), the resultant solution was concentrated under reduced pressure. The residue to which a little amount of water was added was extracted three times with ethyl acetatetetrahydrofuran (1:1). The extract was dried over anhydrous magnesium sulfate and distilled off under reduced pressure to obtain remove the solvent, thereby affording 3-hydroxy-2,2-pentamethylene-1-propanesulfonamide (4.6 g).

NMR(CDCl$_3$)δ: 1.3–1.7(10H,m), 3.33(2H,s), 3.72(2H,s), 5.38(2H,br)

REFERENCE EXAMPLE 3

Production of 3-hydroxy-2,2-tetramethylene-1-propanesulfonamide

The above-identified compound was obtained from 3-bromo-2,2-tetramethylene-1-propanol as the starting material by the same manner as in Reference Example 2.

NMR(CDCl$_3$)δ: 1.68(8H,s), 2.48(1H,brs), 3.30(2H,s) 3.59(2H,s), 6.00(2H,s)

REFERENCE EXAMPLE 4

Production of 3-hydroxy-2,2-trimethylene-1-propanesulfonamide

The above-identified compound was obtained from 3-bromo-2,2-trimethylene-1-propanol as the starting material by the same manner as in Reference Example 2.

NMR(CDCl$_3$)δ: 1.8–2.2(6H,m), 3.45(2H,s), 3.90(2H,s) 5.00(2H,s)

REFERENCE EXAMPLE 5

Production of 3-hydroxy-2,2dimethylene-1-propanesulfonamide

The above-identified compound was obtained from 3-bromo-2,2-dimethylene-1-propanol as the starting material by the same manner as in Reference Example 2.

NMR(CDCl$_3$)δ: 0.6–0.9(4H,m), 3.20(1H,brs), 3.26(2H,s), 3.62(2H,s,J=4.4Hz)

REFERENCE EXAMPLE 6

Production of 3-hydroxy-2,2-(2-oxatrimethylene)-1-propanesulfonamide

The above-identified compound was obtained from 3-bromo-2,2-(2-oxatrimethylene)-1-propanol as the starting material by the same manner as in Reference Example 2.

NMR(CDCl$_3$)δ: 3.64(2H,s), 4.10(2H,d,J=5.6Hz), 4.27(1H,t,J=5.6Hz),4.47(2H,d,J=6.4Hz), 4.66(2H,d,J=6.4Hz),6.38(2H,s)

REFERENCE EXAMPLE 7

Production of 3-hydroxy-2,2-(3-oxapentamethylene)-1-propanesulfonamide

The above-identified compound was obtained from 3-bromo-2,2-(2-oxapentamethylene)-1-propanol as the starting material by the same manner as in Reference Example 2.

NMR(CDCl$_3$)δ:1.5–1.9(4H,m), 3.38(2H,s), 3.6–3.8(4H,m),3.85(2H,s), 4.83(2H,bs)

REFERENCE EXAMPLE 8

Production of 3-bromo-2,2-trimethylene-1-propanesulfonamide a) 3-Hydroxy-2,2-trimethylene-1-propanethiocyanate (8.3 g) and triphenylphosphine (15 g) were dissolved in 1,2-dichloroethane (100 ml) followed by stirring under ice-cooling. To the resultant solution was added N-bromosuccinimide (10.1 g) in small portions. The mixture was stirred for 1.5 hours at room temperature and for 1 hour at 60° C. The reaction mixture was concentrated under reduced pressure and the residue was subjected to a silica gel column chromatography, eluting with hexane-ethyl acetate (9:1). The corresponding fractions were concentrated to obtain 3-bromo-2,2-trimethylene-1-propanethiocyanate (10 g) as oil.

NMR(CDCl$_3$)δ: 1.8–2.2(6H,m), 3.31(2H,s), 3.71(2H,s)

b) 3-Bromo-2,2-trimethylene-1-propanethiocyanate (10 g) was dissolved in acetic acid (40 ml), to which water (80 ml) was added. Chlorine gas was bubbled in the resultant solution for 3 hours at room temperature under stirring. Water (100 ml) was added to the reaction solution, which was then extracted with dichloromethane (50 ml×3). The extract was washed with water, dried and concentrated under reduced pressure. The residue was dissolved in dichloromethane (100 ml), in which ammonia gas was bubbled for 40 minutes. The reaction solution to which ice water (100 ml) was added was extracted three times with dichloromethane (50 ml). The extract was washed with water, dried and concentrated under reduced pressure. The residue was subjected to a silica gel column chromatography, eluting with dichloromethane-ethyl acetate (9:1). The corresponding fractions were concentrated to obtain the above-identified compound (6.25 g) as oil.

NMR(CDCl$_3$)δ: 1.8–2.4(6H,m), 3.54(2H,s), 3.91(2H,s), 3.54(2H,s)

REFERENCE EXAMPLE 9

Production of (4-hydroxymethylcyclohexane-1-yl) methanesulfonamide

The above-identified compound was obtained from (4-bromomethylcyclohexane-1-yl) methanol as the starting material by the same manner as in Reference Example 2.

mp: 146°–149° C.

Elementary Analysis for $C_8H_{17}NO_3S$: Calculated: C,46.35; H,8.27; N,6 76. Found C,46.10; H,8.42; N,6.46.

EXAMPLE 1

Production of 6-[(2,2-pentamethylene-3-sulfamoylpropyl)oxy]imidazo[1,2-b]pyridazine To a solution of 1-hydroxy-2,2-pentamethylene-3-propanesulfonamide (1.25 g) in dimethylacetamide (50 ml) were added sodium hydride (60%, oil) (0.48 g) and 6-chloroimidazo[1,2-b]pyridazine (1.08 g). The mixture was stirred for 7 hours at 70° C. under nitrogen gas atmosphere. After cooling, the mixture was distilled under reduced pressure to remove the solvent. The residue was poured into ice water, and the mixture was adjusted to pH 4.0 with 1 N-hydrochloric acid and extracted with a mixture of ethyl acetate-tetrahydrofuran (2:1) (100 ml×2). The extract was washed with a saturated saline, dried over anhydrous magnesium sulfate and concentrated under reduced pressure. The residue was subjected to a silica gel column chromatography, eluting with chloroform-ethyl acetate-methanol(5:5:1). The corresponding fractions were concentrated to obtain the above-identified compound (0.32 g).

mp: 246°–248° C.

Elementary analysis: $C_{14}H_{20}N_4O_3S$: Calculated (%): C, 51.83; H, 6.21; N, 17.27. Found (%): C, 51.76; H, 6.26; N, 17.25.

EXAMPLE 2

Production of 6-[(2,2-tetramethylene-3-sulfamoylpropyl)oxy]imidazo[1,2-b]pyridazine The above-identified compound (2.02 g) as colorless needles was obtained from 1-hydroxy-2,2-tetramethylene-3-propanesulfonamide (1.94 g), sodium hydride (0.8 g) and 6-chloroimidazo[1,2-b]pyridazine (1.69 g) by the same manner as in Example 1.

mp: 186°–188° C.

Elementary analysis: $C_{13}H_{18}N_4O_3S$: Calculated (%): C, 50.31; H, 5 85; N, 18 05. Found (%) C, 50.52; H, 5.97; N, 17.99.

EXAMPLE 3

Production of 6-[(2,2-trimethylene-3-sulfamoylpropyl)oxy]imidazo[1,2-b]pyridazine The above-identified compound (1.38 g) as colorless needles was obtained from 1-hydroxy-2,2-trimethylene-3-propanesulfonamide (1.44 g), sodium hydride (0.64 g) and 6-chloroimidazo[1,2-b]pyridazine (1.39 g) by the same manner as in Example 1.

mp: 238°–241° C.

Elementary analysis: $C_{12}H_{16}N_4O_3S$: Calculated (%): C, 48.64; H, 5.44; N, 18.91. Found (%): C, 48.64; H, 5.55; N, 18.75.

EXAMPLE 4

Production of 6-[(2,2-dimethylene-3-sulfamoylpropyl)oxy]imidazo[1,2-b]pyridazine The above-identified compound (1.74 g) as colorless needles was obtained from 1-hydroxy-2,2-dimethylene-3-propanesulfonamide (1.39 g), sodium hydride (0.67 g) and 6-chloroimidazo[1,2-b]pyridazine (1.62 g) by the same manner as in Example 1.

mp: 195°–197° C.

Elementary analysis: $C_{11}H_{14}N_4O_3S$: Calculated (%): C, 46.80; H, 5.00; N, 19.84. Found (%) C, 46.69; H, 5.01; N, 19.79.

EXAMPLE 5

Production of 6-[(2,2-pentamethylene-3-sulfamoylpropyl)oxy]imidazo[1,2-b]pyridazine hydrochloride 6-[(2,2-Pentamethylene-3-sulfamoylpropyl)oxy]imidazo[1,2-b]pyridazine (0.38 g) obtained in Example 1 was suspended in ethanol (15 ml), followed by adding 1 N-hydrochloric acid (1.2 ml). The mixture was concentrated and the residue was recrystallized from ethanol (10 ml) to afford the above-identified compound (0.4 g) as colorless needles.

mp: 242°–244° C.

Elementary analysis: $C_{14}H_{20}N_4O_3S \cdot HCl$: Calculated (%): C, 46.60; H, 5.87; N, 15.53. Found (%): C, 46.70; H, 5.92; N, 15.52.

By the same manner as in Example 5, the following compounds of Examples 6 to 8 were obtained.

EXAMPLE 6

Production of 6-[(2,2-tetramethylene-3-sulfamoylpropyl)oxy]imidazo[1,2-b]pyridazine hydrochloride mp: 194°–97° C.

Elementary analysis: $C_{13}H_{18}N_4O_3S \cdot HCl \cdot 3/2H_2O$: Calculated (%): C, 41.77; H, 5.93; N, 14.99. Found (%): C, 41.51; H, 5.63; N, 14.99.

EXAMPLE 7

Production of 6-[(2,2-trimethylene-3-sulfamoylpropyl)oxy]imidazo[1,2-b]pyridazine hydrochloride mp: 215°–218° C.

Elementary analysis: $C_{12}H_{16}N_4O_3S \cdot HCl$: Calculated (%): C, 43.31; H, 5.15; N, 16.84. Found (%): C, 43.50; H, 5.31; N, 16.59.

EXAMPLE 8

Production of 6-[(2,2-dimethylene-3-sulfamoylpropyl)oxy]imidazo[1,2-b]pyridazine hydrochloride mp: 198°–200° C.

Elementary analysis: $C_{11}H_{14}N_4O_3S \cdot HCl$: Calculated (%): C, 41.45; H, 4.74; N, 17.58. Found (%): C, 41.65; H, 4.78; N, 17.33.

EXAMPLE 9

Production of 6-[[2,2-(2-oxatrimethylene)-3sulfamoylpropyl]oxy]imidazo[1,2-b]pyridazine The above-identified compound was obtained from 1-hydroxy-[2,2-(oxatrimethylene)-3-propylsulfonamide and 6-chloroimidazo[1,2-b]pyridazine by the same manner as in Example 1.

mp: 253°–255° C.

Elementary analysis: $C_{11}H_{14}N_4O_4S$: Calculated (%): C, 44.29; H, 4.73; N, 18.78. Found (%): C, 44.52; H, 4.80; N, 18.68.

EXAMPLE 10

Production of 6-[[2,2-(2-oxatrimethylene)-3sulfamoylpropyl]oxy]imidazo[1,2-b]pyridazine hydrochloride The above-identified compound was obtained from the compound obtained in Example 9 by the same manner as in Example 5.

mp: 140°–144° C.

Elementary analysis: $C_{11}H_{14}N_4O_4S \cdot HCl$: Calculated (%): C, 39.39; H, 4.81; N, 16.12. Found (%): C, 39.52; H, 4.78; N, 15.98.

EXAMPLE 11

Production of 6-[[2,2-(3-oxopentamethylene)-3-sulfamoylpropyl]oxy]imidazo[1,2-b]pyridazine The above-identified compound (0.97 g) as colorless needles was obtained from 3-hydroxy-2,2-(3-oxapentamethylene)-1-sulfonamide (1.0 g), sodium hydride (0.4 g) and 6-chloroimidazo[1,2-b]pyridazine (0.85 g) by the same manner as in Example 1.

mp: 233°–235° C.

Elementary analysis: $C_{13}H_{18}N_4O_4S$: Calculated (%): C, 47.84; H, 5.56; N, 17 17. Found (%): C, 47.78; H, 5.57; N, 17.03.

EXAMPLE 12

Production of 6-[[2,2-(3-oxopentamethylene)-3-sulfamoylpropyl]oxy]imidazo[1,2-b]pyridazine hydrochloride The above-identified compound was obtained from the compound obtained in Example 11 by the same manner as in Example 5.

mp: 225°–228° C.

Elementary analysis: $C_{13}H_{18}N_4O_4S \cdot HCl$: Calculated (%): C, 43.03; H, 5.28; N, 15.44. Found (%): C, 43.20; H, 5.58; N, 15.11.

EXAMPLE 13

Production of 6-[(2,2-trimethylene-3-sulfamoylpropyl)thio]imidazo[1,2-b]pyridazine 3-Bromo-2,2-trimethylene-3-propanesulfonamide (1.6 g) was dissolved into methanol (20 ml), to which 2 N-potassium hydrogensulfide ethanolic solution (14 ml) was added and refluxed for 2.5 hours under nitrogen gas atmosphere. After ice-cooling, 1 N-sodium methoxide methanolic solution (7 ml) and 6-chloroimidazo[1,2-b]pyridazine (1.08 g) were added to the reaction solution and refluxed for 2.5 hours under nitrogen gas atmosphere. The reaction solution was concentrated under reduced pressure and the residue was poured into ice water (10 ml). The mixture was adjusted to pH 6.0 by adding 1 N-hydrochloric acid and then extracted twice with ethyl acetate (50 ml). The extract was washed with water, dried and concentrated under reduced pressure. The residue was subjected to a silica gel column chromatography, eluting with dichloromethaneethyl acetate-methanol(10:10:1). The corresponding fractions were concentrated to obtain the above-identified compound (1.56 g) as colorless needles.

mp: 161°–164° C.

Elementary analysis: $C_{12}H_{16}N_4O_2S_2$: Calculated (%): C, 46.13; H, 5.16; N, 17.93. Found (%): C, 46.38; H, 5.24; N, 17.85.

EXAMPLE 14

Production of 6-[(2,2-(trimethylene-3-sulfamoylpropyl)thio]imidazo[1,2-b]pyridazine hydrochloride The above-identified compound was obtained from the compound obtained in Example 13 by the same manner as in Example 5.

mp: 188°–191° C.

Elementary analysis: $C_{12}H_{16}N_4O_2S_2 \cdot HCl \cdot 0.3C_2H_5OH$: Calculated (%) C, 41.73; H, 5.23; N, 15.50. Found (%): C, 41.97; H, 5.15; N, 15.50.

EXAMPLE 15

Production of 6-[(2,2-trimethylene-3-sulfamoylpropyl)thio]imidazo[1,2-b]pyridazine A mixture of 6-mercaptoimidazo[1,2-b]pyridazine (1.5 g) and 1 N-sodium methoxide methanolic solution (10 ml) together with a solution of 3-bromo-2,2-trimethylene-3-propanesulfonamide (2.4 g) in methanol (50 ml) were refluxed for 2 hours. The reaction solution was concentrated under reduced pressure and the residue was poured into ice water (10 ml). The mixture was adjusted to pH 6.0 with 1 N-hydrochloric acid and extracted three times with ethyl acetate (50 ml). The extract was washed with water, dried and concentrated under reduced pressure. The residue was subjected to a silica gel column chromatography, eluting with dichloromethane-ethyl acetate-methanol (10:10:1). The corresponding fractions were concentrated to obtain the same compound (2.3 g) as obtained in Example 13.

EXAMPLE 16

Production of 6-[(4-sulfamoylmethylcyclohexane-1-yl)methyloxy]imidazo[1,2-b]pyridazine hydrochloric acid salt A mixture of (4-hydroxymethylcyclohexane-1-yl)methanesulfonamide (0.58 g), sodium hydride (0.23 g), 6-chloroimidazo[1,2-b]pyridazine (0.43 g) and dimethylformamide (20 ml) was stirred for 3 hours at 85°–90° C. The reaction solution was concentrated under reduced pressure and the residue was poured into water (20 ml). The mixture was adjusted to pH 7.0 with 1 N-hydrochloric acid. The precipitated crystals were collected by filtration and recrystallized from a mixture of ethanol and ethyl ether to afford the above-identified compound (0.44 g).

mp: 191°–194° C.

Elementary analysis: $C_{14}H_{20}N_4O_3S$: Calculated (%): C, 51.83; H, 6.21; N, 17.27. Found (%) C, 51.87; H, 6.50; N, 16.87.

EXAMPLE 17

Production of 6-[[2,2-(N-benzyloxycarbonyl)-2-azatrimethylene)-3-sulfamoylpropyl]oxy]imidazo [1,2-b]pyridazine The above-identified compound as colorless crystals was obtained from 3-hydroxy-2,2-(N-benzyloxycarbonyl-2-azatrimethylene)-1-propanol (0.48 g) and 6-chloroimidazo[1,2-b]pyridazine (0.26 g) by the same manner as in Example 1.

NMR(CDCl$_3$)δ: 3.62(2H,s), 3.8–4.3(4H,m), 4.62(2H,s) 5.05(1H,s), 5.13(1H,s), 6.80(1H,d,J=9.8Hz), 7.10(2H,s), 7.3–7.6(5H,m), 7.61(1H,s), 8.01(1H,d,J=9.8Hz), 8.07(1H,s)

EXAMPLE 18

Production of 6-[[2,2-(2-azatrimethylene)-3-sulfamoylpropyl]oxy]imidazo[1,2-b]pyridazine 6-[(2,2-N-benzyloxycarbonyl-2-azatrimethylene)-3-sulfamoylpropyl)oxy]imidazo[1,2-b]pyridazine hydrochloride (0.36 g) was suspended in methanol (20 ml), to which 1 N-hydrochloric acid (1.7 ml) and 10% palladium on carbon (100 mg) were added, the catalytic reduction was conducted at 40° to 50° C. After completing the reduction, the catalyst was removed and the filtrate was concentrated. The residue was recrystallized from a mixture of ethanol and ethyl ether to afford the above-identified compound (0.24 g) as colorless needles.

mp: 180°–183° C.

Elementary analysis: $C_{11}H_{15}N_5O_3S \cdot 2HCl \cdot \frac{1}{2}H_2O \cdot C-H_3OH$: Calculated (%): C, 34.89; H, 5.09; N, 17.69. Found (%): C, 34.92; H, 5.07; N, 17.56.

EXAMPLE 19

Production of 3-methyl-6-[(2,2-pentamethylene-3-sulfamoylpropyl)oxy]imidazo[1,2-b]pyridazine The above-identified compound as colorless crystals was obtained from 1-hydroxy-2,2-pentamethylene-3-propanesulfonamide and 6-chloro-3-methylimidazo[1,2-b]pyridazine by the same manner as in Example 1.

mp: 244° C.

Elementary analysis: $C_{15}H_{22}N_4O_3S$: Calculated (%): C, 53.24; H, 6.55; N, 16.56. Found (%): C, 53.17; H, 6.47; N, 16.57.

EXAMPLE 20

Production of 3-chloro-6-[(2,2-pentamethylene-3-sulfamoylpropyl)oxy]imidazo[1,2-b]pyridazine The above-identified compound as colorless crystals was obtained from 1-hydroxy-2,2-pentamethylene-3-propanesulfonamide and 3,6-dichloroimidazo[1,2-b]pyridazine by the same manner as in Example 1.

mp: 244° C.

Elementary analysis: $C_{14}H_{19}N_4O_3SCl$: Calculated (%): C, 46.86; H, 5.34; N, 15.61. Found (%): C, 46.54; H, 5.25; N, 15.43.

PREPARATION EXAMPLE

| a) Coated tablets | |
|---|---|
| Compound of Example 1 | 10.0 mg |
| Lactose | 60.0 mg |
| Cornstarch | 35.0 mg |
| Gelatin | 3.0 mg |
| Magnesium stearate | 2.0 mg |

A mixture of Compound of Example 1, lactose and cornstarch was mixed with 10% gelatin aqueous solution and passed through a filter (1 mm mesh) to obtain granules. The granules were dried at 40° C. and again screened. The resulting granules were mixed with magnesium stearate and compressed. The resulting core tablets were coated an aqueous suspension of sucrose, titanium dioxide, talc and acacia as a sugar coating material in accordance with a conventional method. The coated tablets were glazed with yellow beeswax.

| b) Tablets | |
|---|---|
| Compound of Example 1 | 10.0 mg |
| Lactose | 70.0 mg |
| Cornstarch | 50.0 mg |
| Soluble Starch | 7.0 mg |
| Magnesium Stearate | 3.0 mg |
| Total | 140.0 mg |

A mixture of Compound of Example 1 and magnesium stearate was mixed with an aqueous soluble starch solution and granulated. The granules were dried and blended with lactose and cornstarch. The blend was compressed into tablets.

| c) Solution for injection | |
|---|---|
| Compound of Example 1 | 5.0 mg |
| Sodium chloride | 20.0 mg |
| Distilled water | added to 2.0 ml |

Compound of Example 1 and sodium chloride were dissolved in distilled water, to which further distilled water was added up to the prescribed concentration. The resulting solution was filtered and packed into 2 ml of ampoules under a sterile condition. The ampoules were sterilized and sealed. Each of ampoules contained 5 mg of Compound of Example 1.

The results of pharmacological tests on representative compounds of this invention are shown below.

METHOD OF MEASUREMENT

Effect on Bronchoconstriction Induced by Platelet Activating Factor (PAF) in Guinea Pigs Male Hartley guinea pigs (body weight 500 g) were used. The bronchoconstriction reaction in the guinea pig which has intravenously received PAF (1 $\mu$g/Kg) was measured by the Konzett-Rössler method. The trachea of the guinea pig with its back fixed was incised under anesthesia condition with urethane (intraperitoneal injection, 1.50 g/Kg) and connected with an artificial respirator via a cannula. The branch of the tracheal cannula was connected with a transducer (7020 type, Ugobasile). Air was sent to the trachea at the volume of 3-7 ml/stroke, at the stroke of 70 strokes/min. at load pressure of 10 cm $H_2O$ to lung and overflowed air volume was recorded with Rectegraph (Recte-Hori-8s, Sanei Sokuki) via the transducer. After the guinea pig was treated with galamine (1 mg/Kg, i.v.), PAF (1 $\mu$g/Kg) dissolved in a physiological saline solution was administered to the guinea pig via a jugular venous cannula and the bronchoconstriction reaction induced thereby was recorded for 15 minutes. The drug (10 mg/Kg) suspended in a 5% gum arabic solution was administered orally 1 hour before the injection of PAF. The results are shown in the following Table I.

TABLE I

| Example No. | Inhibition (%) of PAF-induced bronchoconstriction |
|---|---|
| 1 | 72 |
| 2 | 78 |
| 3 | 58 |
| 4 | 48 |
| 9 | 51 |
| 13 | 40 |

As is clear from the above Table, I, the compound (I) of the present invention possess excellent controlling effects for airway construction and can be used as antiasthmatics.

What is claimed is:

1. An imidazo [1,2-b]pyridazine compound of the formula (I):

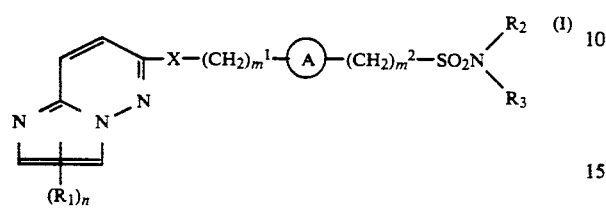

or a pharmaceutically acceptable salt thereof, wherein:

$R_1$ is halogen or a lower alkyl group optionally substituted with one to four substituents selected from the group consisting of hydroxy, amino, mono-lower alkylamino, lower alkoxy and halogen;

$R_2$ and $R_3$ are independently selected from the group consisting of hydrogen; a lower alkyl group optionally substituted with one to four substituents selected from the group consisting of hydroxy, amino, mono-lower alkylamino, lower alkoxy and halogen; a cycloalkyl group; and a phenyl group optionally substituted with one to five substituents selected from the group consisting of amino, mono-lower alkylamino, di-lower alkylamino, lower alkoxy and halogen; or $R_2$ and $R_3$ together with the adjacent nitrogen atom to which they are bonded form a four to seven membered heterocyclic ring having carbon atoms, at least one nitrogen atom and optionally oxygen or sulfur atoms as constituent atoms of the heterocyclic ring, said heterocyclic ring being unsubstituted or substituted with one to five substituents selected from the group consisting of hydroxy, amino, mono-lower alkylamino, di-lower alkylamino, lower alkoxy and halogen;

X is an oxygen atom or $S(O)_k$ wherein k is 0 to 2;

group -Ⓐ- is a bivalent three to seven membered carbocyclic or heterocyclic group, said heterocyclic group having carbon atoms and at least one oxygen, sulfur or nitrogen atoms as constituent atoms of the ring, wherein said carbocyclic or heterocyclic group is unsubstituted or substituted with one to five substituents selected from the group consisting of a lower alkyl group optionally substituted with one to four substituents selected from the group consisting of hydroxy, an amino group, mono-lower alkylamino, lower alkoxy and halogen; an amino group; a mono-$C_{1-4}$ alkylamino group; a di-$C_{1-4}$ alkylamino group; a five- to seven-membered cyclic amino group having carbon atoms and at least one nitrogen atom as constituent ring atoms; an amido group; a $C_{1-4}$ acylamido group; hydroxy; a lower alkoxy group; and halogen;

$m^1$ and $m^2$ are independently an integer of 0 to 4; and n is 0 or 1.

2. A compound of claim 1 wherein group -Ⓐ- is a bivalent three to six membered cycloalkylene group, n is 0 or 1, $R^1$ is a lower alkyl group, X is an oxygen atom or a sulfur atom, $m^1$ and $m^2$ are independently 1 or 2 and $R^2$ and $R^3$ are each hydrogen, or a pharmaceutically acceptable salt thereof.

3. A compound of claim 2 in which the three to six membered cycloalkylene group is

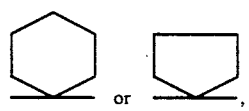

or a pharmaceutically acceptable salt thereof.

4. A compound of claim 1 wherein group -Ⓐ- is a bivalent three to six membered cycloalkylene group, n is 0, X is an oxygen atom, $m^1$ and $m^2$ are each 1 and $R^2$ and $R^3$ are each hydrogen, or a pharmaceutically acceptable salt thereof.

5. A compound of claim 1 in which the three to six membered cycloalkylene group is

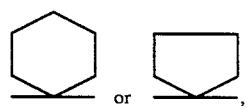

or a pharmaceutically acceptable salt thereof.

6. A compound of claim 1 wherein group -Ⓐ- is a bivalent $C_{3-7}$ monocyclic hydrocarbon group.

7. A compound of claim 6 wherein the bivalent monocyclic hydrocarbon group is selected from the group consisting of

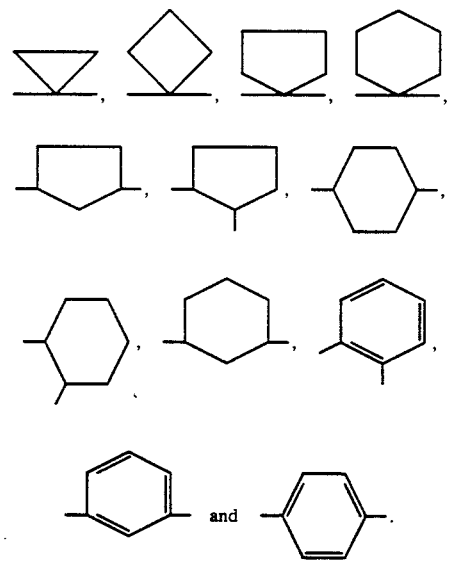

8. A compound of claim 1 wherein group -Ⓐ- is a bivalent heterocyclic group selected from the group consisting of

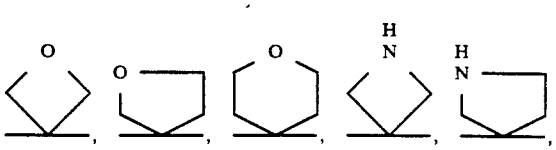

-continued

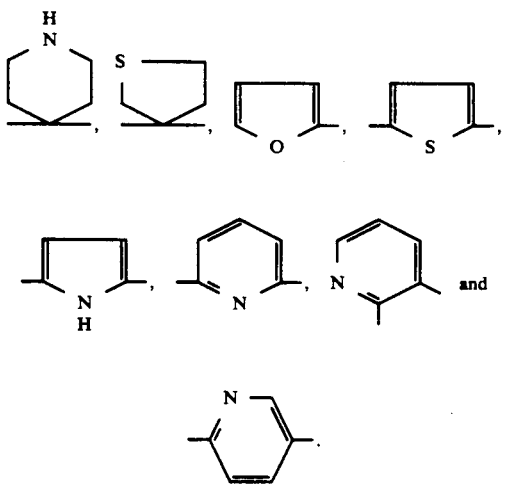

9. A compound of claim 1 wherein $R_2$ and $R_3$ together with the adjacent nitrogen atom to which they are bonded form a heterocyclic ring selected from the group consisting of pyrrolidino, piperidino, morpholino, piperazino and homopiperazino.

10. The compound 6-[(2,2-pentamethylene-3-sulfamoylpropyl)oxy]imidazo [1,2-b]pyridazine or the hydrochloride salt thereof.

11. The compound 6-[(2,2-tetramethylene-3-sulfamoylpropyl)oxy]imidazo [1,2-b]pyridazine or the hydrochloride salt thereof.

12. An antiasthmatic composition which comprises a compound of the formula (I) claimed in claim 1 or its pharmaceutically acceptable salt and a pharmaceutically acceptable carrier or diluent.

13. A method of treating asthma which comprises administering a therapeutically effective amount of a compound of the formula (I) claimed in claim 1 or its pharmaceutically acceptable salt, optionally together with a pharmaceutically acceptable carrier or diluent, to mammals.

14. A method of treating asthma which comprises administering a therapeutically effective amount of a compound as claimed in claim 2 to a mammal in need thereof.

15. A method of treating asthma which comprises administering a therapeutically effective amount of a compound as claimed in claim 4 to a mammal in need thereof.

16. A method of treating asthma which comprises administering a therapeutically effective amount of a compound as claimed in claim 4 to a mammal in need thereof.

* * * * *